(12) United States Patent
Park et al.

(10) Patent No.: US 11,442,054 B2
(45) Date of Patent: Sep. 13, 2022

(54) PIPETTE TYPE PATCH CLAMP, MEASURING DEVICE HAVING THE PATCH CLAMP, AND METHOD OF MANUFACTURING THE PATCH CLAMP

(71) Applicant: Industry-Academic Cooperation Foundation, Dankook University, Gyeonggi-do (KR)

(72) Inventors: Jae-Hyoung Park, Gyeonggi-do (KR); Yoon Jae Nam, Gyeonggi-do (KR); Seung-Ki Lee, Seoul (KR)

(73) Assignee: Industry-Academic Cooperation Foundation, Dankook University, Gyeonggi-do (KR)

( * ) Notice: Subject to any disclaimer, the term of this patent is extended or adjusted under 35 U.S.C. 154(b) by 551 days.

(21) Appl. No.: 16/535,423

(22) Filed: Aug. 8, 2019

(65) Prior Publication Data

US 2020/0348283 A1 Nov. 5, 2020

(30) Foreign Application Priority Data

Mar. 26, 2019 (KR) .................. 10-2019-0034448
Aug. 6, 2019 (KR) .................. 10-2019-0095754

(51) Int. Cl.
*G01N 33/487* (2006.01)
*B01L 3/02* (2006.01)

(52) U.S. Cl.
CPC ........ *G01N 33/48728* (2013.01); *B01L 3/021* (2013.01); *B01L 2200/0668* (2013.01); *B01L 2300/0645* (2013.01)

(58) Field of Classification Search
CPC ........ G01N 33/48728; G01N 33/5014; G01N 33/5026; B01L 3/021; B01L 2200/0668; B01L 2300/0645; C12M 21/08; C12M 23/12; C12M 23/34; C12M 25/04; C12M 29/05; C12M 33/00; C12N 5/0062; B33Y 10/00; B33Y 30/00; B33Y 70/00; B33Y 80/00

See application file for complete search history.

(56) References Cited

U.S. PATENT DOCUMENTS

2002/0063067 A1* 5/2002 Bech ............... G01N 33/48728
205/450
2004/0146849 A1* 7/2004 Huang ............ G01N 33/48728
435/287.1

* cited by examiner

*Primary Examiner* — Michael L Hobbs
(74) *Attorney, Agent, or Firm* — Meunier Carlin & Curfman LLC

(57) ABSTRACT

Disclosed are a pipette type patch clamp, a measuring device having the patch clamp, and a method of manufacturing the patch clamp. The pipette type patch clamp includes a pipette type puller having a through region with a predetermined length such that an object is sucked therethrough, a silicon wafer configured to support the puller, an insulating layer disposed on a surface of the silicon wafer and a surface of the puller, and an electrode layer disposed on a surface of the insulating layer to connect to a first fluid channel and a second fluid channel.

8 Claims, 20 Drawing Sheets

<Before suction>
Low resistance

<After suction>
Giga-seal formation

PIPETTE TYPE PATCH CLAMP, MEASURING DEVICE HAVING THE PATCH CLAMP, AND METHOD OF MANUFACTURING THE PATCH CLAMP

CROSS-REFERENCE TO RELATED APPLICATION(S)

This application claims the priority benefit of Korean Patent Application No. 10-2019-0034448 filed on Mar. 26, 2019, and Korean Patent Application No. 10-2019-0095754 filed on Aug. 6, 2019, in the Korean Intellectual Property Office, the disclosures of which are incorporated herein by reference for all purposes.

BACKGROUND

1. Field of the Invention

One or more example embodiments relate to a pipette type patch clamp, a measuring device having the patch clamp, and a method of manufacturing the patch clamp, and more particularly, to a patch clamp which may automatically capture a predetermined object such as a cell, and a method of manufacturing the patch clamp.

2. Description of the Related Art

One of basic methods for drug development and disease research is electrically measuring reactions of living cells to external stimuli. As one method, a patch clamp may be used to electrically measure reactions of living cells.

The patch clamp is a device used to capture a single cell or a tissue membrane and measure ion current or voltage for studying electrophysiological characteristics thereof.

A scheme of using the existing patch clamp requires specialized skill and sophisticated equipment for a person to directly attach a microtube made of glass to a cell. In this example, it takes more time for the operation, and thus the existing scheme is applicable only to a single cell or very few cells.

Further, existing patch clamps are manufactured two at a time, and thus the yield is low. In addition, in response to changes in external conditions such as temperature and humidity at a time of manufacturing a patch clamp, the shape of the patch clamp may change. Due to the varying shape of the patch clamp manufactured in a situation in which the external conditions change, serious errors may occur during an operation of the patch clamp measuring minute current or voltage.

To solve the foregoing issues, a patch clamp that may faster and automatically capture a number of cells and accurately measure reactions of the cells is needed.

SUMMARY

An aspect provides a pipette type patch clamp and a method of manufacturing the patch clamp using a semiconductor process.

Another aspect also provides a pipette type patch clamp that may automatically capture a cell and measure ion current and voltage of a single cell or a tissue membrane without requiring specialized skill, and a method of manufacturing the patch clamp.

According to an aspect, there is provided a measuring device including a patch clamp, a first fluid channel disposed on the top of the patch clamp, and a second fluid channel disposed on the bottom of the patch clamp, wherein the patch clamp may include a puller having a through region with a predetermined length such that an object may be sucked therethrough, a silicon wafer configured to support the puller, an insulating layer disposed on a surface of the silicon wafer and a surface of the puller, and an electrode layer disposed on a surface of the insulating layer.

The puller may have the through region penetrating between a first site in which the first fluid channel is positioned and a second site in which the second fluid channel is positioned.

The puller may be formed in a shape of a pipette through a plurality of reflow processes.

The insulating layer may be disposed on the surface of the silicon wafer and the surface of the puller.

According to another aspect, there is provided a patch clamp including a puller having a through region with a predetermined length such that an object may be sucked therethrough, a silicon wafer configured to support the puller, an insulating layer disposed on a surface of the silicon wafer and a surface of the puller, and an electrode layer disposed on a surface of the insulating layer to connect to a first fluid channel disposed on the top of the patch clamp and a second fluid channel disposed on the bottom of the patch clamp.

The puller may be formed in a shape of a pipette through a plurality of reflow processes.

The insulating layer may be disposed on the surface of the silicon wafer and the surface of the puller.

According to another aspect, there is provided a method of manufacturing a patch clamp, the method including a first step of etching a peripheral region of a first type filler while leaving the first type filler in a silicon wafer in a downward direction from a top surface of the silicon wafer, a second step of bonding a glass wafer to the top surface of the silicon wafer, a third step of forming a first type puller by filling the peripheral region etched in the first step with glass through a reflow process of the glass wafer, wherein the filler of the silicon wafer may be positioned at a center of the first type puller, a fourth step of etching a peripheral region of the puller in the silicon wafer, after removing the glass wafer present on the top surface of the silicon wafer, a fifth step of forming a second type puller from the first type puller by additionally performing a reflow of glass on the first type puller, a sixth step of etching the filler of the silicon wafer positioned at a center of the second type puller, a seventh step of etching in an upward direction from a bottom surface of the silicon wafer to the bottom of the second type puller, an eighth step of disposing an insulating layer on the top surface of the silicon wafer, the bottom surface of the silicon wafer, and a surface of the second type puller, and a ninth step of disposing an electrode layer on a surface of the insulating layer.

A width of the peripheral region etched in the first step may correspond to a width of the second type puller.

A height of the peripheral region etched in the fourth step may correspond to a height of the second type puller.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
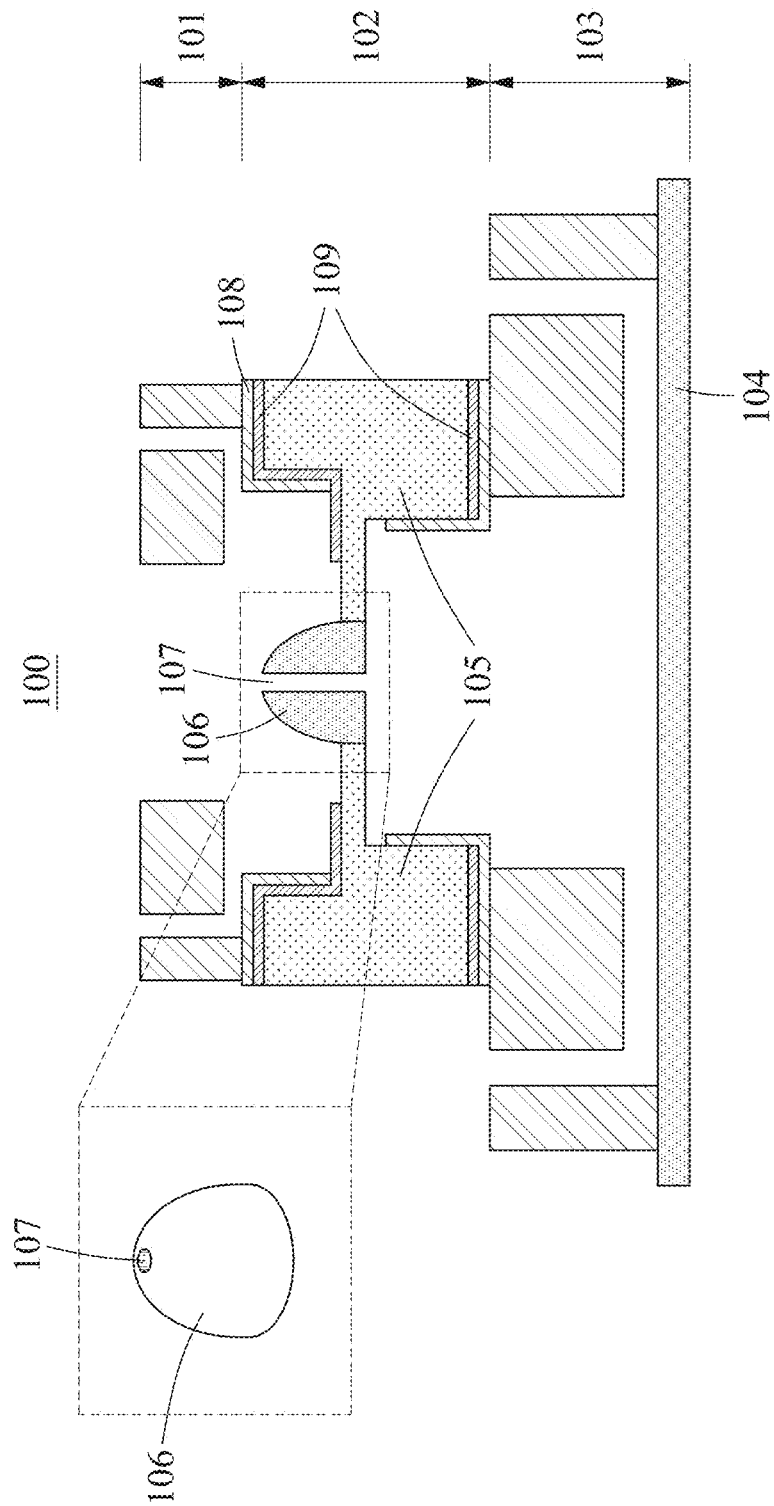
FIG. 1 illustrates a measuring device having a pipette type patch clamp according to an example embodiment.

Hereinafter, some example embodiments will be described in detail with reference to the accompanying drawings. Like reference numerals in the drawings refer to like elements throughout the present disclosure. Various modifications may be made to the example embodiments. Here, the examples are not construed as limited to the disclosure and should be understood to include all changes, equivalents, and replacements within the idea and the technical scope of the disclosure. Although terms of "first," "second," and the like are used to explain various components, the components are not limited to such terms. These terms are used only to distinguish one component from another component.

The terminology used herein is for the purpose of describing particular embodiments only and is not intended to be limiting. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Hereinafter, example embodiments will be described in detail with reference to the accompanying drawings.

One or more example embodiments relate to a pipette type patch clamp and a method of manufacturing the patch clamp using a semiconductor process. According to the example embodiments, a measuring device having a patch clamp may be provided by coupling a micro patch clamp to polydimethylsiloxane (PDMS) channels. The measuring device manufactured according to the example embodiments may automatically capture a cell and fast measure ion current and voltage of a single cell or a tissue membrane without requiring specialized skill.

According to the example embodiments, a puller may be formed by forming a predetermined type filler, for example, a cylindrical filler, in a silicon wafer and then filling a space formed by etching a periphery of the filler with a material such as glass through a reflow process. A pipette type patch clamp may be formed by additionally etching a periphery of the puller including glass and performing a reflow thereon. In this example, a through region may be formed by etching an inner portion of the puller positioned at a center of the pipette type puller, and a hole may be formed in the pipette type patch clamp through the through region.

FIG. 1 illustrates a measuring device having a pipette type patch clamp according to an example embodiment.

Referring to FIG. 1, a measuring device 100 may be configured by coupling a patch clamp 102 to an upper fluid channel 101 and a lower fluid channel 103. The upper fluid channel 101 and the lower fluid channel 103 may include a clear material such as polydimethylsiloxane (PDMS).

The pipette type patch clamp 102 may include a pipette type puller 106. A hole 107 may be disposed at a center of the puller 106. A width of a top part of the pipette type puller 106 may be less than a width of a bottom part thereof. The top part may have a round shape such as an arch. The shape of the top part may be adjusted through a secondary reflow process.

The measuring device 100 may capture a cell through the hole 107 provided in the pipette type puller 106, and inject an extracellular solution into the captured cell via a through region through the hole 107. The patch clamp 102 may be configured in the form in which an insulating layer 109 and an electrode layer 108 are stacked on a silicon wafer 105 formed of silicon.

A method of manufacturing the pipette type patch clamp 102 will be described in detail with reference to FIGS. 5A through 11.

Figure 2:
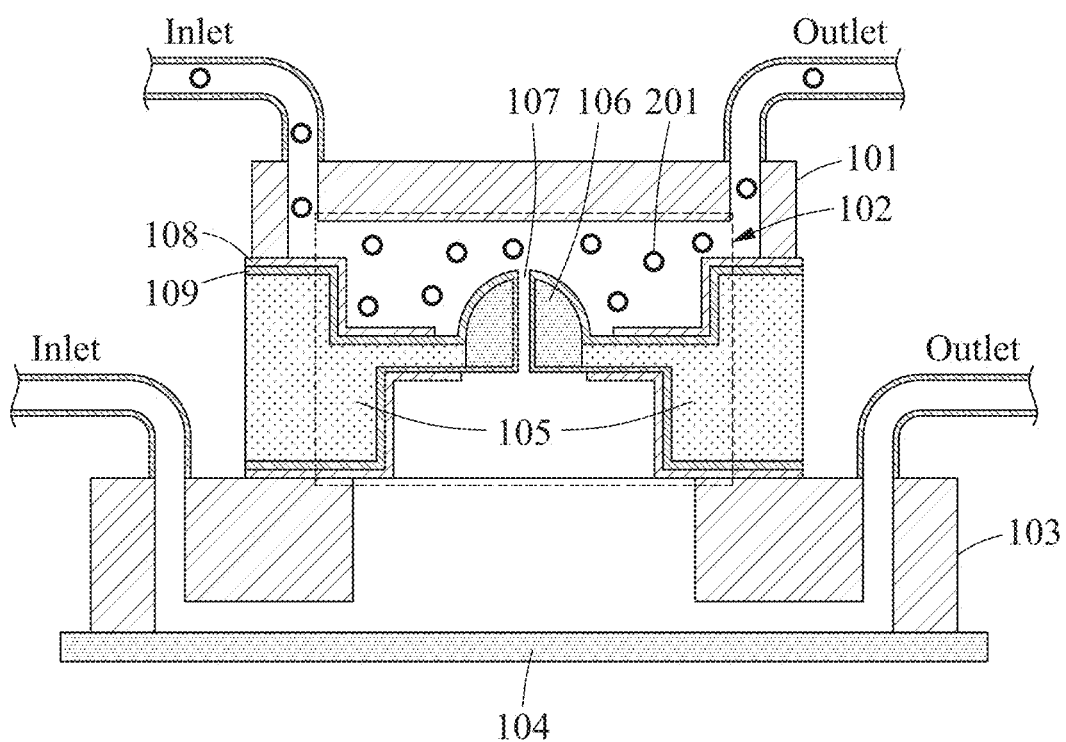
FIG. 2 illustrates a measuring device in which a patch clamp and fluid channels are coupled according to an example embodiment.

FIG. 2 illustrates a measuring device in which a patch clamp and fluid channels are coupled according to an example embodiment.

Referring to FIG. 2, a process of injecting a solution including an object 201 such as a cell to be tested into the upper fluid channel 101 included in the measuring device 100 of FIG. 1 through an inlet is illustrated.

A solution including an object such as a cell may be injected through the inlet of the upper fluid channel 101 and discharged through an outlet thereof. When a pressure is applied to the patch clamp 102 while the solution including the cell flows from the inlet toward the outlet, the cell included in the solution may be moved to the hole 107 of the puller 106 provided in the patch clamp 102.

Through this, the pipette type patch clamp 102 may automatically capture the cell included in the solution much more easily than when a worker manually captures the cell.

An external material may be injected into the lower fluid channel 103 positioned under the patch clamp 102 through an inlet and discharged through an outlet. When an electric field is applied to the cell captured in the hole 107 of the puller 106 through the electrode layer 108, a cell membrane may be instantly perforated such that the external material present in the lower fluid channel 103 may be injected into the perforated cell via the through region through the hole 107. In doing so, a current and a voltage when the external material stimulates the cell may be measured.

Figure 3:
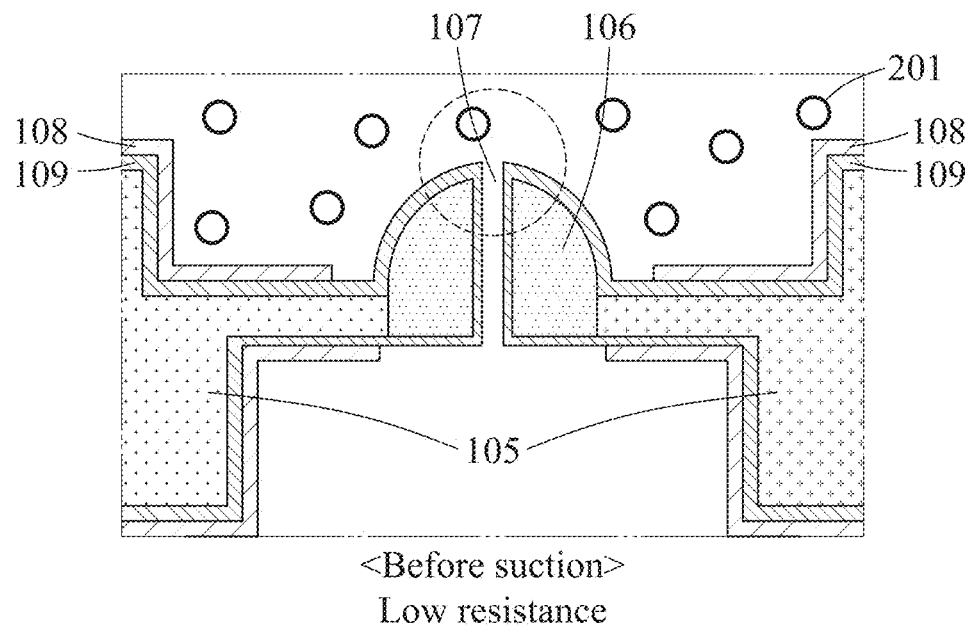
FIG. 3 illustrates a state before a pipette type patch clamp captures a cell according to an example embodiment.
Figure 4:
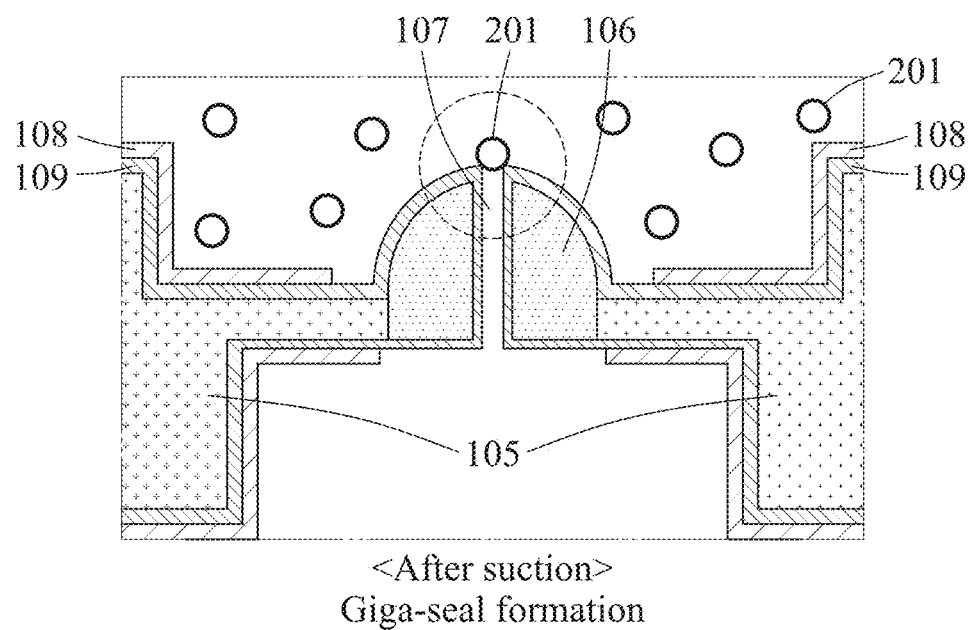
FIG. 4 illustrates a state immediately after a pipette type patch clamp captures a cell according to an example embodiment.

FIG. 3 illustrates a state before a pipette type patch clamp captures a cell according to an example embodiment, and FIG. 4 illustrates a state immediately after the pipette type patch clamp captures a cell according to an example embodiment.

Referring to FIG. 3, a solution including a cell 201 may be injected into the upper fluid channel 101. In this example, the cell 201 is not captured in the hole 107 of the puller 106 through suction, and thus a low resistance may be exhibited.

Meanwhile, referring to FIG. 4, the cell 201 present in the solution in the upper fluid channel 101 may be captured in the hole 107 of the puller 106 through suction. Then, the cell 201 may block the hole 107 such that a gigaseal may be formed. Thus, the example of FIG. 4 exhibits a higher seal resistance than the example of FIG. 3.

According to an example embodiment, effects of a cell ion channel on a predetermined drug may be verified based on voltages and currents measured before and after a hole of a patch clamp is blocked.

Figure 6A:
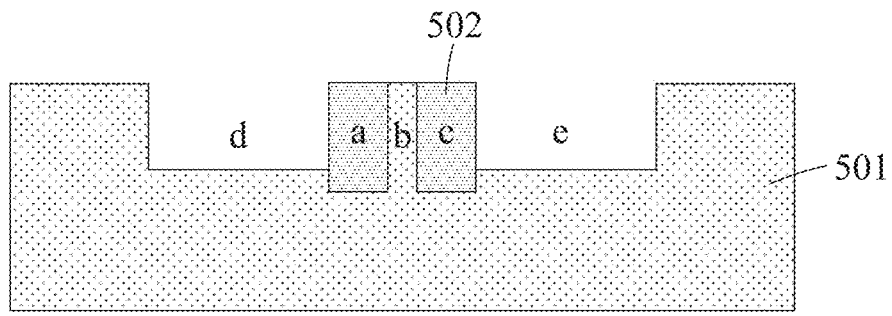
Figure 6B:
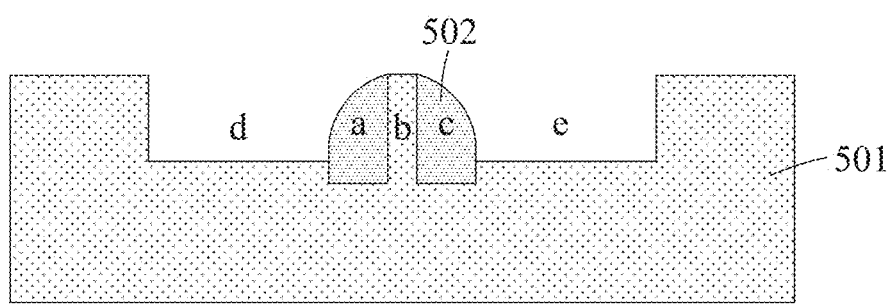
Figure 6C:
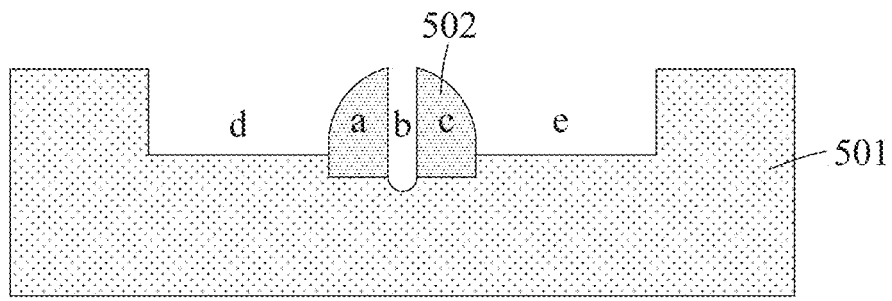
Figure 6D:
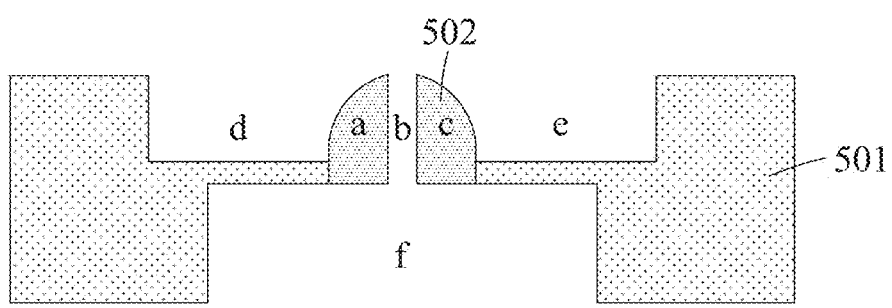
Figure 7A:
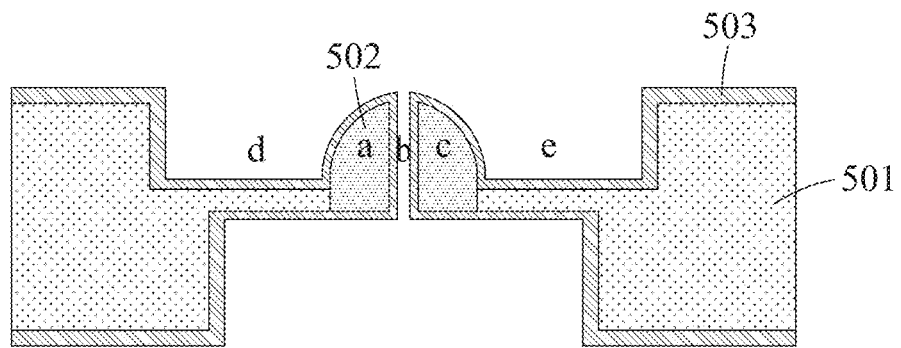
Figure 7B:
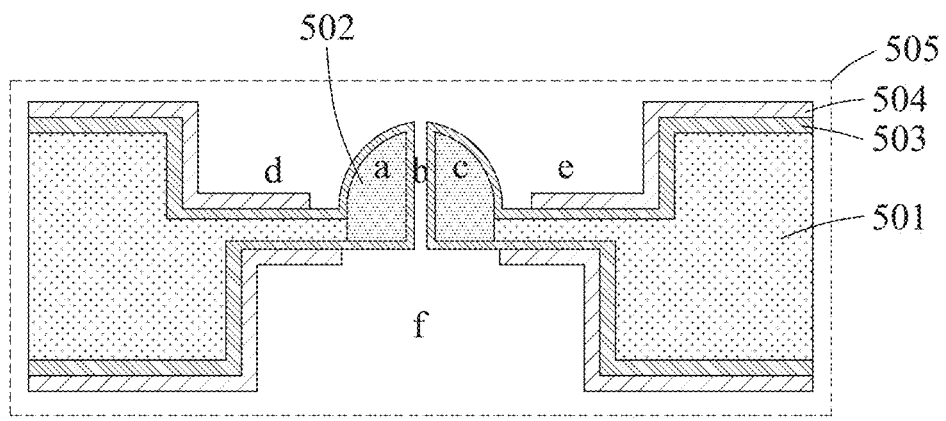
Figure 8A:
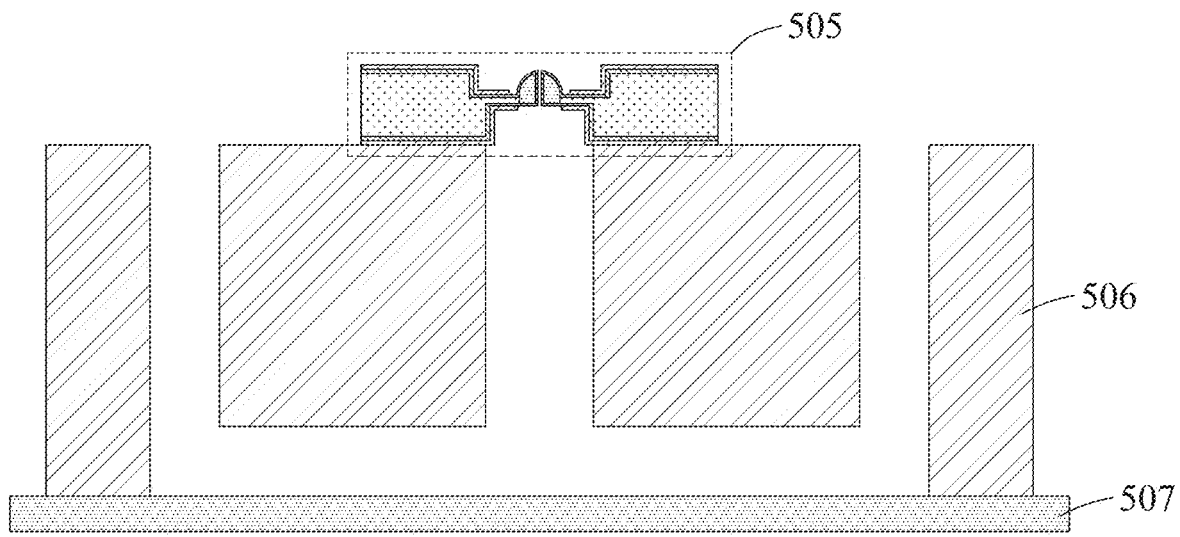
FIGS. 8A and 8B illustrate a process of manufacturing a measuring device in which the pipette type patch clamp manufactured in FIGS. 7A and 7B and fluid channels are coupled according to an example embodiment.
Figure 8B:
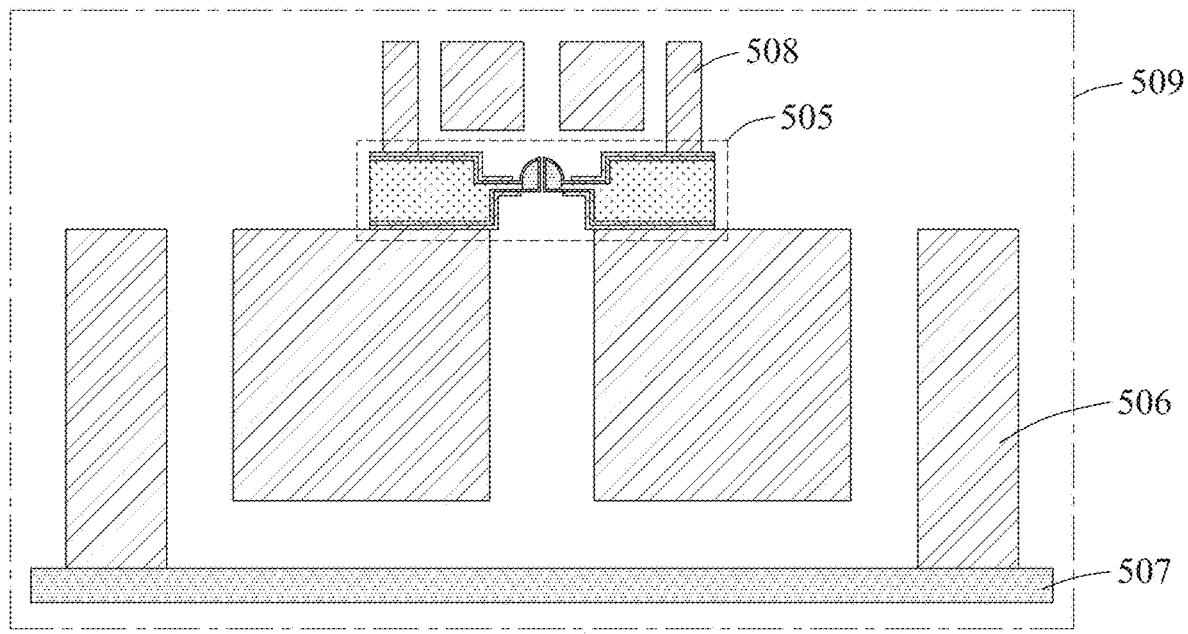

FIGS. 5A through 7B illustrate a process of manufacturing a pipette type patch clamp according to an example embodiment, and FIGS. 8A and 8B illustrate a process of manufacturing a measuring device in which the pipette type patch clamp manufactured in FIGS. 7A and 7B and fluid channels are coupled according to an example embodiment.

Etching processes described with reference to FIGS. 5A through 6D may first pattern a photosensitizer and etch a region in which the photosensitizer is absent. The etching processes may employ etching schemes such as deep reactive-ion etching (DRIE) and reactive-ion etching (RIE). However, example embodiments are not limited thereto.

Figure 5A:
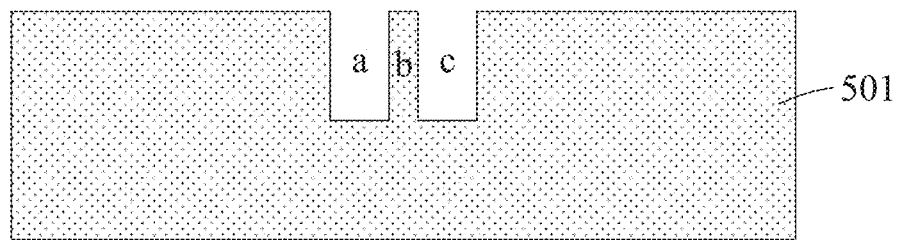
FIGS. 5A through 7B illustrate a process of manufacturing a pipette type patch clamp according to an example embodiment.

Referring to Step 1 of FIG. 5A, a predetermined type filler b may be left on a silicon wafer 501, and a peripheral region a and a peripheral region c of the predetermined type filler b of the silicon wafer 501 may be etched. In this example, a size of a patch site may be determined to be a diameter of the predetermined type filler b, and a size of a puller included in a patch clamp may be determined to be a width of the etched peripheral region a and a width of the etched peripheral region c. Here, the predetermined type filler may be a cylindrical filler. However, example embodiments are not limited thereto. The predetermined type filler may include any filler in a structure with a height, for example, a cylindrical structure, or a polygonal-prismatic structure. The filler may have a top part and a bottom part which are the same or different in length.

Figure 5B:
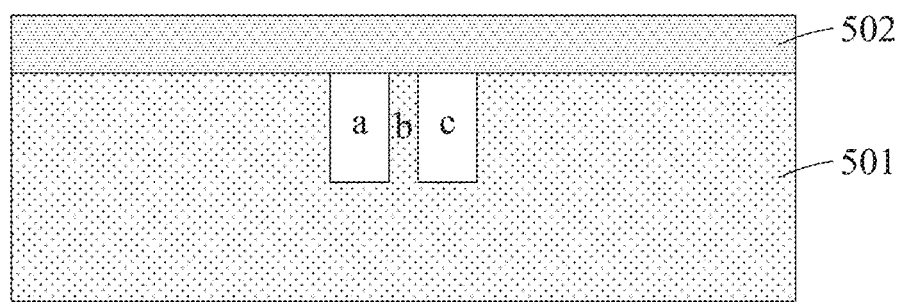

Referring to Step 2 of FIG. 5B, a glass wafer 502 may be bonded to the top of the silicon wafer 501. In this example, the silicon wafer 501 and the glass wafer 502 may be anodically bonded while the peripheral region a and the peripheral region c are in a vacuum state, such that the etched peripheral region a and the etched peripheral region c may be filled with glass of the glass wafer 502.

Figure 5C:
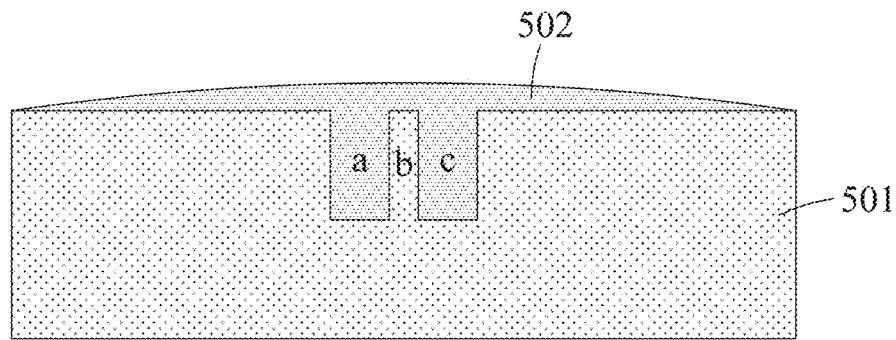

Referring to Step 3 of FIG. 5C, a process of filling the peripheral region a and the peripheral region c adjacent to the cylindrical filler b with the glass of the glass wafer 502 through a primary reflow process is illustrated. Glass of the glass wafer 502 may flow into the peripheral region a and the peripheral region c which are in the vacuum state such that the peripheral region a and the peripheral region c may be filled with glass. Through this, a cylindrical puller including glass may be formed.

Figure 5D:
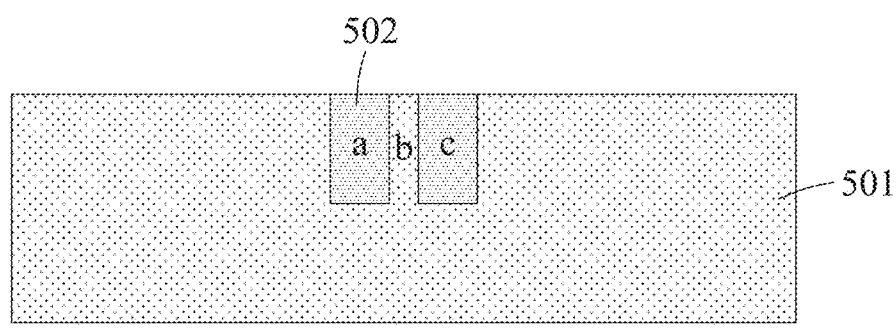

Referring to Step 4 of FIG. 5D, when the peripheral region a and the peripheral region c are filled with glass through the primary reflow process, the glass wafer 502 on the top of the silicon wafer 501 may be removed by chemical polishing or mechanical polishing.

Referring to Step 5 of FIG. 6A, a peripheral region d and a peripheral region e of the cylindrical puller 502 which fills the peripheral region a and the peripheral region c may be etched. Here, an etching depth may be a height of the pipette type puller included in the patch clamp.

Referring to Step 6 of FIG. 6B, the pipette type puller 502 may be formed by applying a secondary reflow process to the predetermined type puller 502, for example, the cylindrical puller. In this example, the pipette type puller 502 may be formed differently depending on a duration of the secondary reflow process. For example, when the duration of the secondary reflow process increases, a slope of the pipette type puller 502 may become relatively gentle.

Referring to Step 7 of FIG. 6C, the predetermined type filler b present at the center of the pipette type puller 502 may be removed. When the filler b is removed, a through region with a predetermined length may be formed in the puller 502.

Referring to Step 8 of FIG. 6D, a lower region f may be formed by performing an etching process in an upward direction from a bottom surface of the silicon wafer 501. In this example, the etching process may be performed until the bottom surface of the silicon wafer 501 reaches the pipette type puller 502. Then, the through region b present at the center of the puller 502 and the etched lower region f may be connected to each other.

Referring to Step 9 of FIG. 7A, an insulating layer 503 may be disposed on the top surface and the bottom surface of the silicon wafer 501 and the surface of the pipette type puller 502. Here, the insulating layer 503 may be stacked on the top surface and the bottom surface of the silicon wafer 501 and the surface of the pipette type puller 502 through a deposition process. In this example, the insulating layer 503 may include a polymer such as parylene. However, example embodiments are not limited thereto.

Referring to Step 10 of FIG. 7B, an electrode layer 504 may be disposed on a portion of a top surface and a bottom surface of the insulating layer 503 stacked in Step 9. Here, the electrode layer 504 may be disposed on a portion of the top surface and the bottom surface of the insulating layer 503 through a deposition process.

Through the process of FIGS. 5A through 7B, a patch clamp 505 having the pipette type puller 502 may be formed finally.

FIGS. 8A and 8B illustrate a process of forming a measuring device 509 through the patch clamp 505 formed through the process of FIGS. 5A through 7B. An order of Step 11 of FIG. 8A and Step 12 of FIG. 8B may change during the process of manufacturing the measuring device 509.

Referring to Step 11 of FIG. 8A, a lower fluid channel 506 may be coupled to the bottom of the patch clamp 505. In this example, the lower fluid channel 506 may include a clear material such as PDMS. However, example embodiments are not limited thereto. The lower fluid channel 506 may include an inlet through which an external material of a cell is injected, and an outlet through which the external material is discharged. A glass substrate 507 may be disposed on the bottom of the lower fluid channel 506.

Meanwhile, referring to Step 12 of FIG. 8B, an upper fluid channel 508 may be coupled to the top of the patch clamp 505. In this example, the upper fluid channel 508 may include a clear material such as PDMS. However, example embodiments are not limited thereto.

Figure 9:
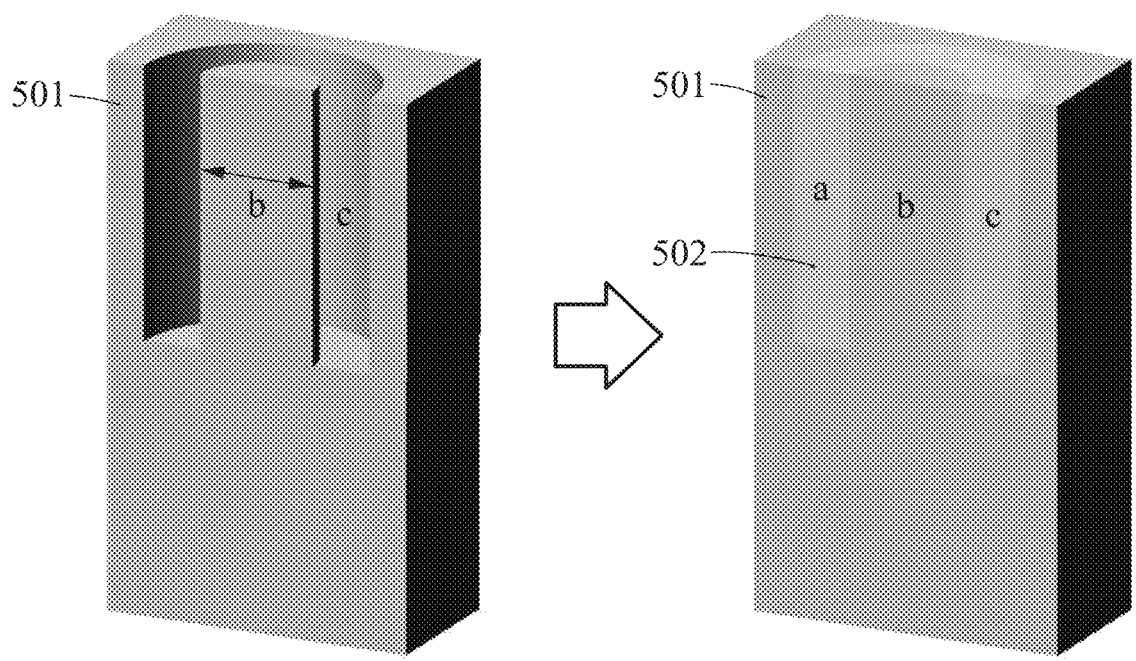
FIGS. 9 through 11 illustrate a process of manufacturing a pipette type patch clamp according to an example embodiment.
Figure 10:
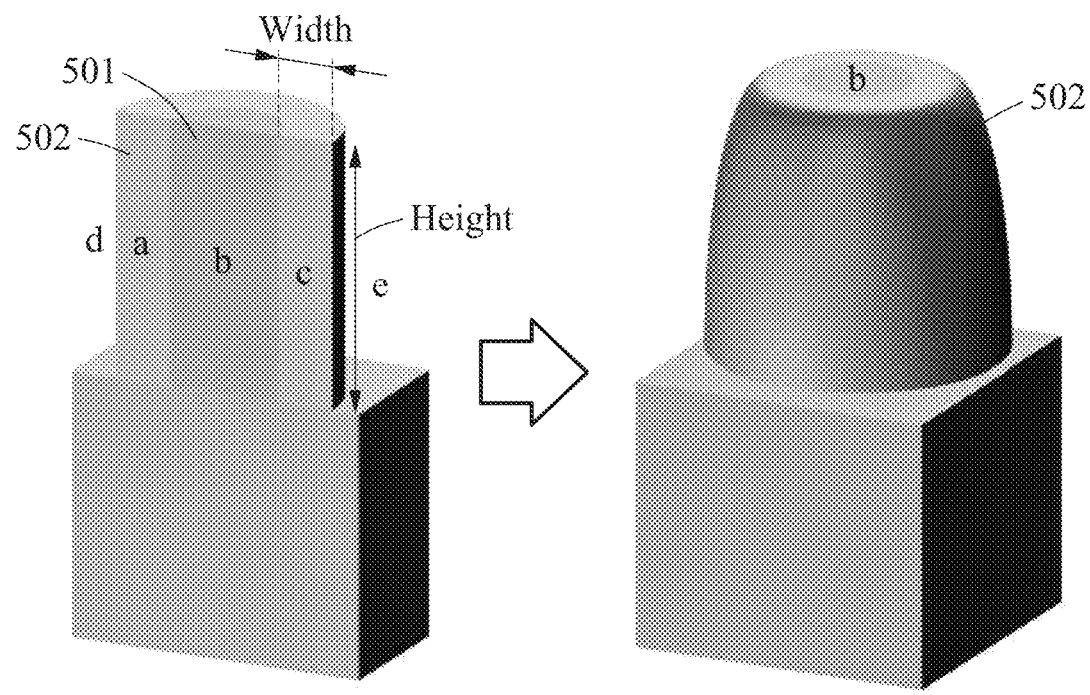
Figure 11:
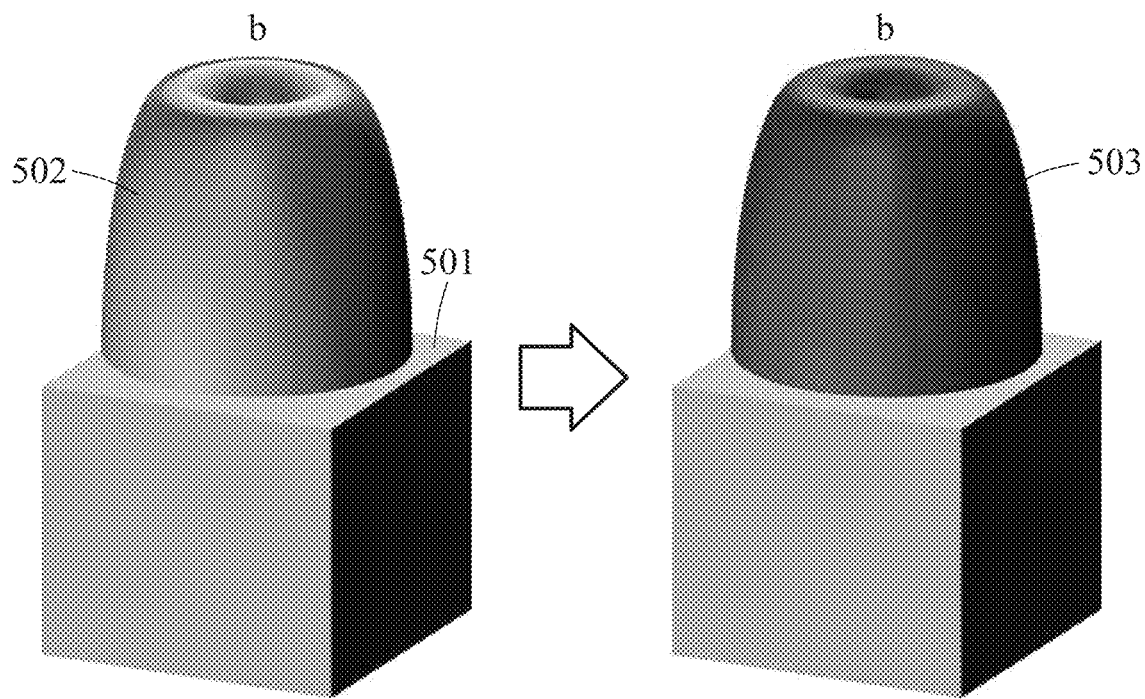
Figure 12A:
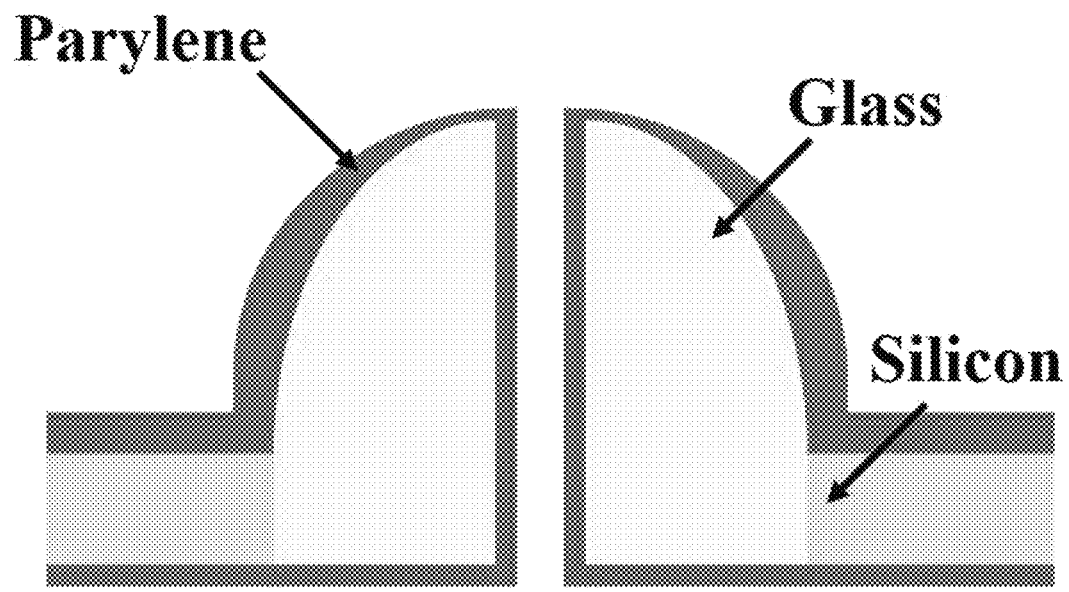
FIGS. 12A through 12D illustrate a practical example of a pipette type patch clamp according to an example embodiment.
Figure 12B:
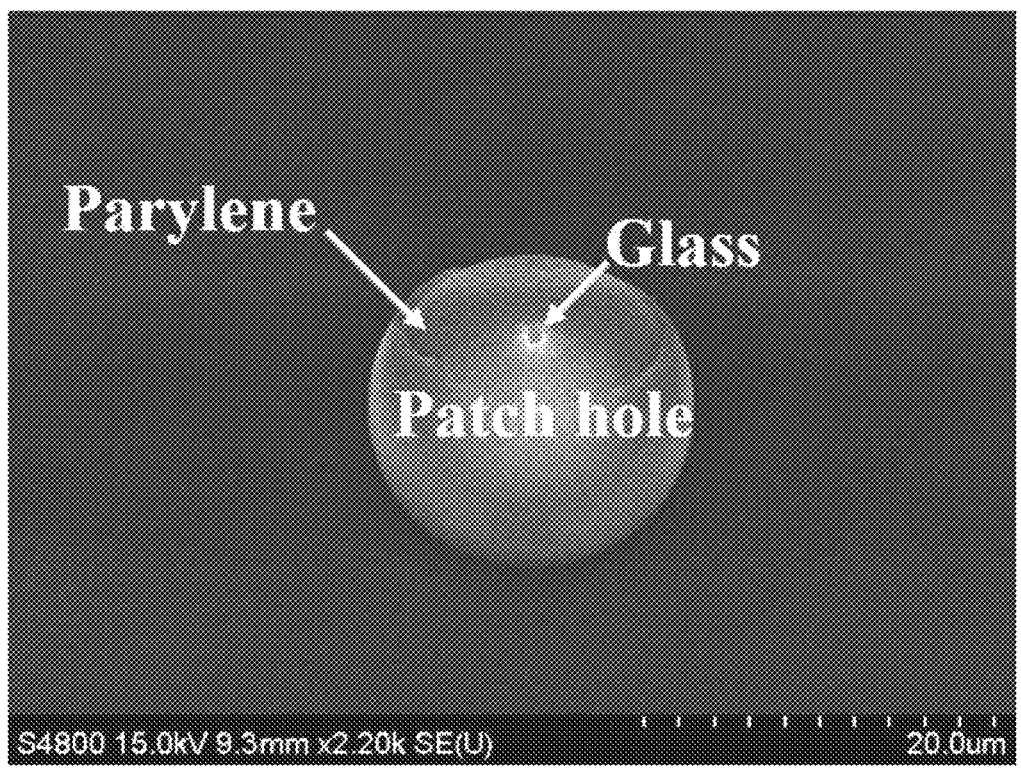
Figure 12C:
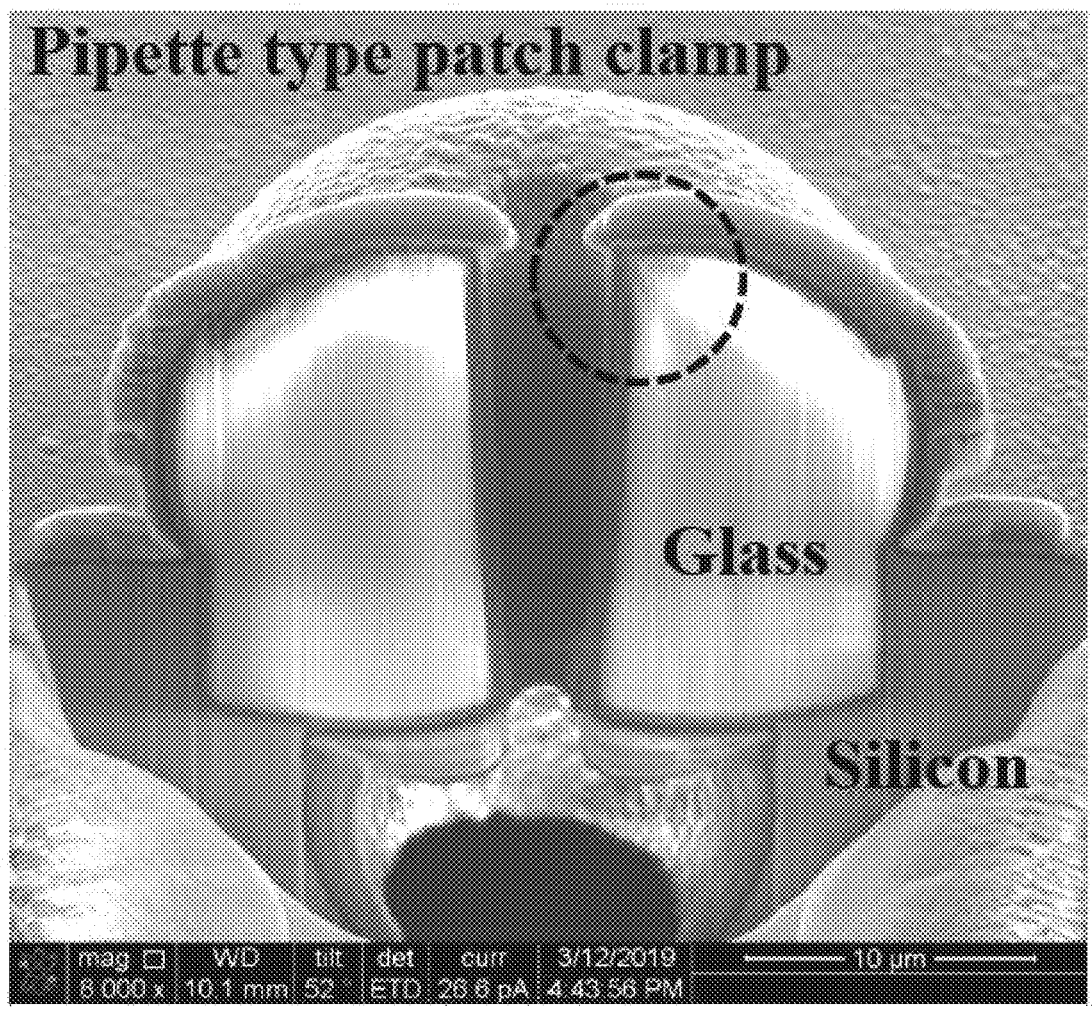
Figure 12D:
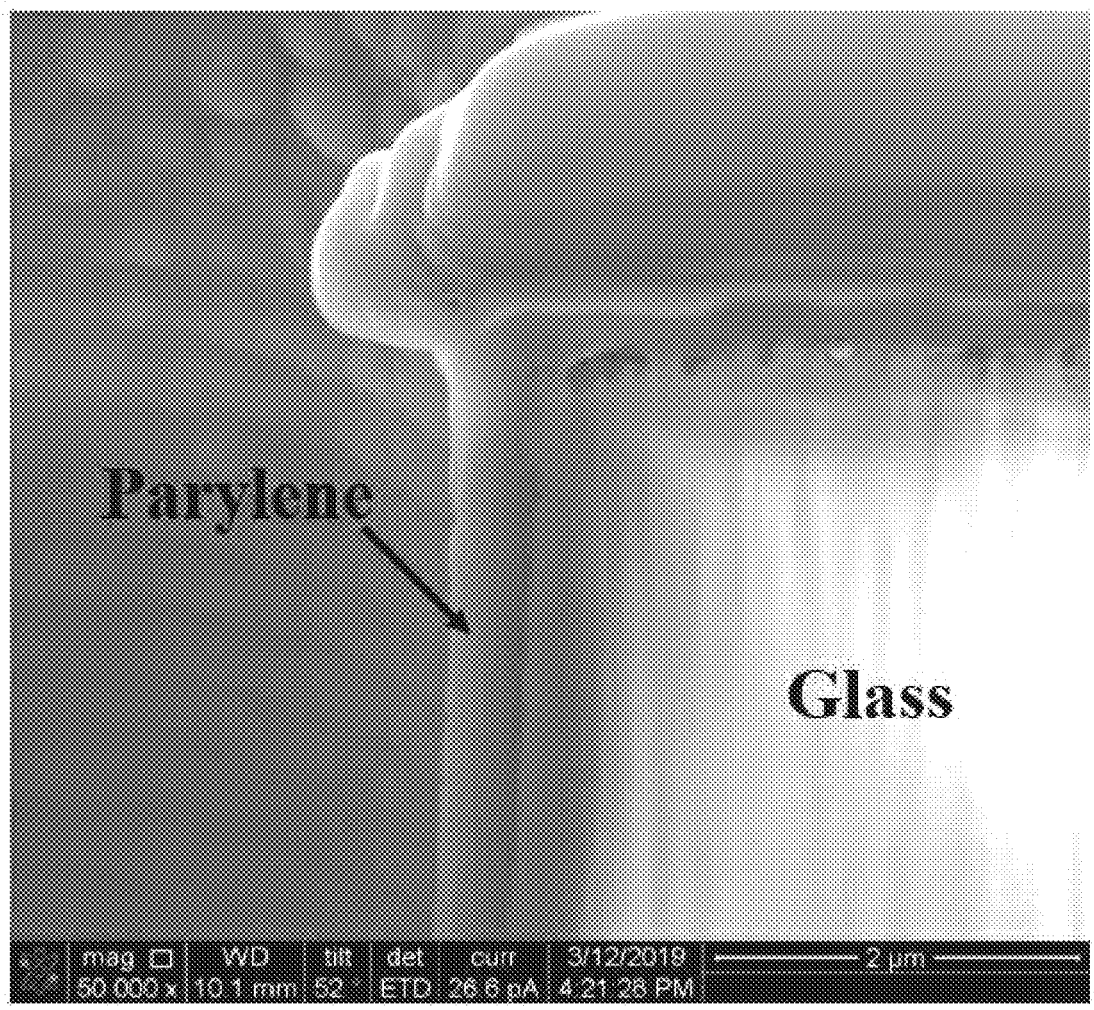

FIGS. 9 through 11 illustrate a process of manufacturing a pipette type patch clamp according to an example embodiment.

A left image of FIG. 9 illustrates a result of performing Step 1 of FIG. 5A, and a right image of FIG. 9 illustrates a result of performing Step 2 through Step 4 of FIGS. 5B through 5D.

In the left image of FIG. 9, the peripheral region a and the peripheral region c of the filler b may be etched while leaving the predetermined type filler b in the silicon wafer 501. In this example, a remaining portion, except for the peripheral region a and the peripheral region c, may be patterned by a photosensitizer. Then, an empty space may be formed in the peripheral region a and the peripheral region c, as shown in the left image of FIG. 9.

As shown in the right image of FIG. 9, the glass wafer 502 may be bonded to the top of the silicon wafer 501 while the peripheral region a and the peripheral region c are in a vacuum state, and the peripheral region a and the peripheral region c being emptied may be filled with glass through the primary reflow process on the glass wafer 502. That is, when the peripheral region a and the peripheral region c being an empty space are filled with glass, the predetermined type puller 502 may be formed.

A left image of FIG. 10 illustrates a result of etching the peripheral region d and the peripheral region c of the predetermined type puller 502, and a right image of FIG. 10 illustrates a process of forming the pipette type puller 502 through the secondary reflow process on the predetermined type puller 502. In this example, the left image of FIG. 10 illustrates a result of performing Step 5 of FIG. 6A, and the right image of FIG. 10 illustrates a result of performing Step 6 of FIG. 6B.

Referring to the left image of FIG. 10, a result of etching the peripheral region d and the peripheral region c of the predetermined type puller 502 to a height is illustrated. Here, the height corresponds to a height of the puller 502. Further, a bottom width of the peripheral region a and the peripheral region c corresponds to a bottom width of the puller 502.

Referring to the right image of FIG. 10, the pipette type puller 502 may be formed by introducing glass to flow in the predetermined type puller 502 through the secondary reflow process.

A left image of FIG. 11 illustrates a result of etching the predetermined type filler b positioned at the center of the pipette type puller 502, and a right image of FIG. 11 illustrates a result of depositing the insulating layer 503 on the pipette type puller 502. In this example, the left image of FIG. 11 illustrates a result of performing Step 7 of FIG. 6C, and the right image of FIG. 11 illustrates a result of performing Step 9 of FIG. 7A.

Referring to the left image of FIG. 11, the predetermined type filler b positioned at the center of the pipette type puller 502 may be etched. Then, a hole may be formed at the center of the pipette type puller 502. Referring to the right image of FIG. 11, the insulating layer 503 may be disposed on the surface of the pipette type puller 502 through deposition. In this example, the insulating layer 503 may include a polymer such as parylene. An initial size of the hole positioned at the center of the puller 502 may correspond to a size of the etched predetermined type filler b. After that, the size of the hole positioned at the center of the puller 502 may be exquisitely adjusted based on a thickness of the insulating layer 503 deposited on the surface of the pipette type puller 502.

FIGS. 12A through 12D illustrate a practical example of a pipette type patch clamp according to an example embodiment.

Referring to FIGS. 12A through 12D, a patch clamp having a pipette type puller is illustrated. The puller may be formed of glass. An outer side of the puller may be supported through a silicon wafer. Meanwhile, a hole may be formed at a center of the puller, and an insulating layer including an insulating material such as parylene may be deposited on a surface of the puller.

In this example, a size of the hole formed at the center of the puller may be determined differently based on a thickness of the insulating layer. Further, a width of the puller and the pipette shape of the puller may be determined based on a duration of the secondary reflow process. Meanwhile, a height of the puller may be determined based on an etching depth of a peripheral region adjacent to the puller.

Figure 13:
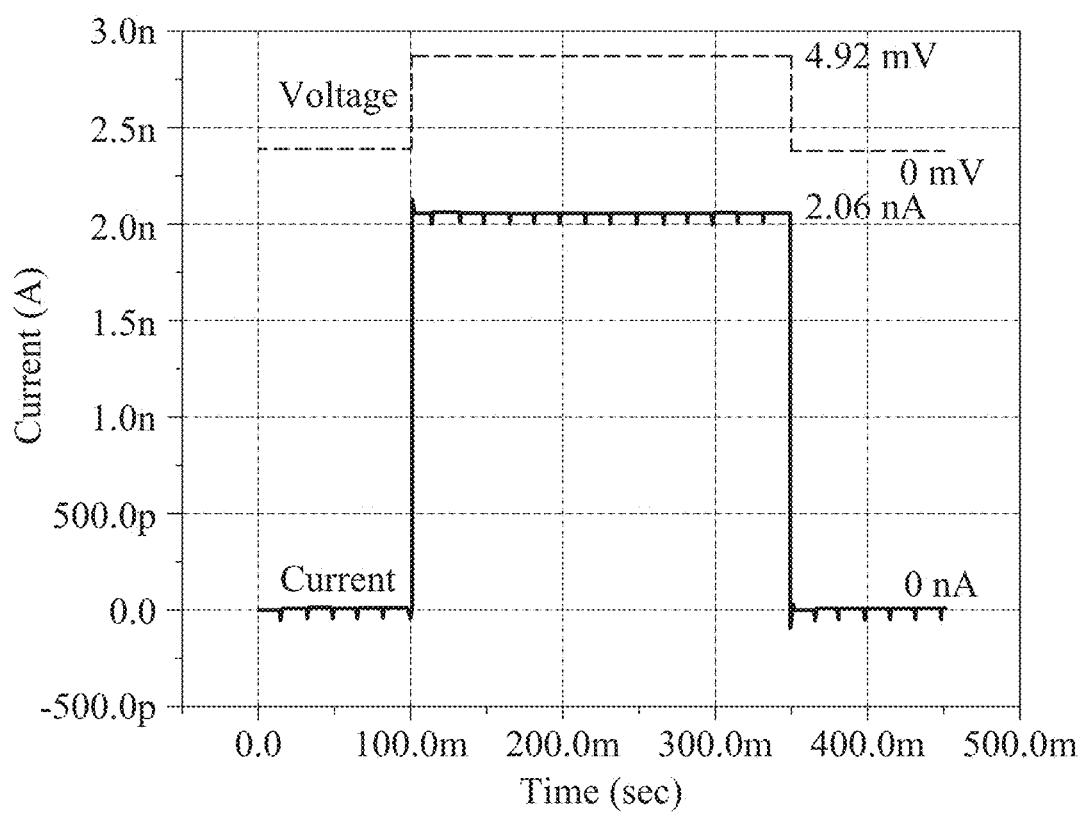
FIG. 13 illustrates a voltage and a current measured before a pipette type patch clamp captures a cell according to an example embodiment.
Figure 14A:
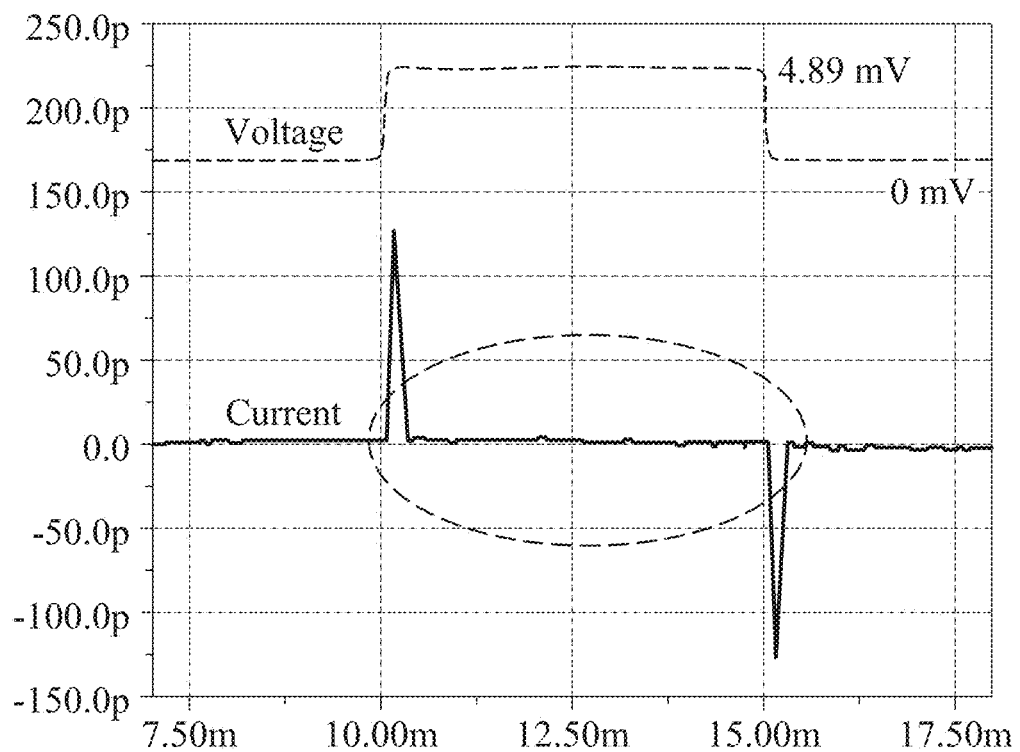
FIGS. 14A and 14B illustrate a voltage and a current measured after a pipette type patch clamp captures a cell according to an example embodiment.
Figure 14B:
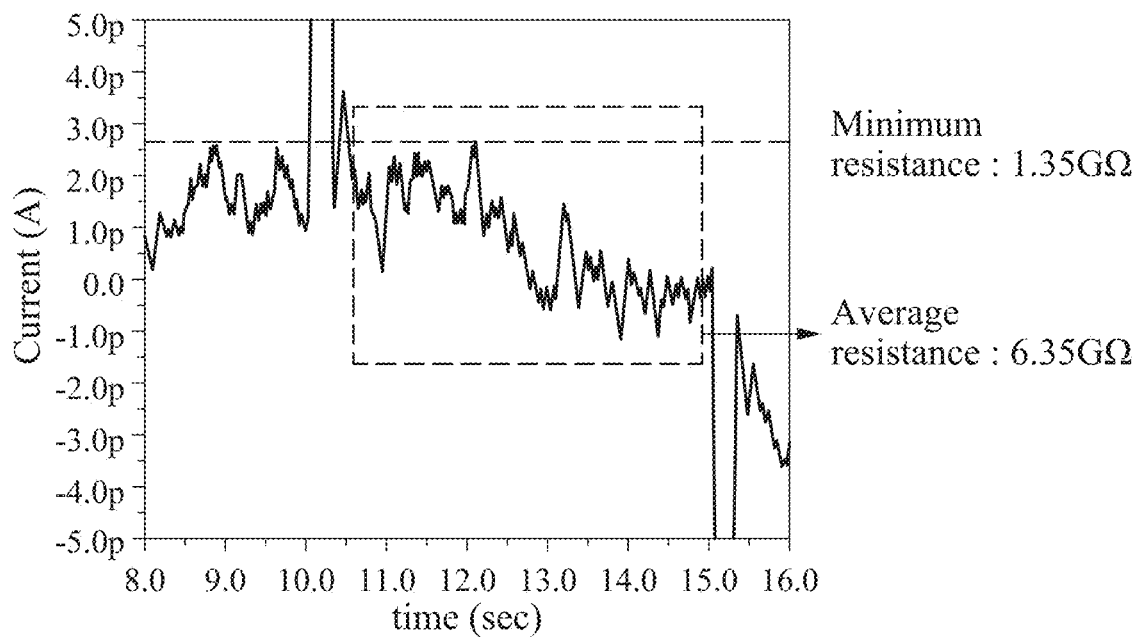

FIG. 13 illustrates a voltage and a current measured before a pipette type patch clamp captures a cell according to an example embodiment, and FIGS. 14A and 14B illustrate a voltage and a current measured after the pipette type patch clamp captures a cell according to an example embodiment.

FIG. 13 illustrates an example in which a cell included in a solution present in an upper fluid channel does not block a hole of a puller of a pipette type patch clamp. FIGS. 14A and 14B illustrate an example in which a cell included in the solution present in the upper fluid channel is captured by the pipette type patch clamp through suction and blocks the hole of the puller of the pipette type patch clamp.

Through the voltages or the currents measured in the examples of FIGS. 13 and 14A and 14B, a sealing resistance occurring when the cell blocks the hole may be verified. It may be verified from FIGS. 13 and 14A and 14B that when the cell is captured in the hole of the puller through suction and seals the hole of the puller, the sealing resistance increases.

According to example embodiments, a shape or a size of a pipette type patch clamp may be determined flexibly based on a diameter of a predetermined type filler left in a silicon wafer, a thickness of glass filling a peripheral region of the filler, and an etching depth of the peripheral region of the filler.

According to example embodiments, when a pipette type patch clamp is coupled to an upper fluid channel and a lower fluid channel, a cell in a solution injected into the upper fluid channel may be automatically captured. Thus, a measuring device that may guarantee convenience while not requiring specialized skill may be provided.

Further, an intracellular solution and an extracellular solution may be more easily exchanged through the upper fluid channel and the lower fluid channel of the measuring device, whereby a high throughput may be achieved.

According to example embodiments, at a time of manufacturing a pipette type puller through a semiconductor process, the puller may be processed in a shape appropriate for a predetermined cell by adjusting a size or a shape of the puller.

According to example embodiments, a chip type patch clamp may be manufactured uniformly and fast through a semiconductor process.

According to example embodiments, patch clamps may be manufactured as independent elements in a form of an array, and thus it is possible to measure independent signals or form individual electrodes with respect to the plurality of patch clamps.

According to example embodiments, a patch clamp may be simply manufactured using isotropic etching using SF6, aeolotropic DRIE which is a semiconductor process, and a plurality of reflow processes of glass, whereby a chip including a micro-type patch clamp with a high yield may be manufactured at low cost.

According to example embodiments, a pipette type patch clamp may be manufactured, and thus a sealing resistance higher than that of a planar patch clamp may be achieved.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

What is claimed is:

1. A measuring device having a patch clamp, the measuring device comprising:
    a patch clamp;
    a first fluid channel disposed on the top of the patch clamp; and
    a second fluid channel disposed on the bottom of the patch clamp,
        wherein the patch clamp comprises:
        a puller having a through region with a predetermined length such that an object is sucked therethrough;
        a silicon wafer configured to support the puller;
        an insulating layer disposed on a surface of the silicon wafer and a surface of the puller; and
        an electrode layer disposed on a surface of the insulating layer,
        wherein the puller is formed in a shape of a pipette through a plurality of reflow processes, and wherein a width of a top part of the puller is less than a width of a bottom part of the puller.

2. The measuring device of claim 1, wherein the puller has the through region penetrating between a first site in which the first fluid channel is positioned and a second site in which the second fluid channel is positioned.

3. The measuring device of claim 1, wherein the insulating layer is disposed on the surface of the silicon wafer and the surface of the puller.

4. A patch clamp, comprising:
    a puller having a through region with a predetermined length such that an object is sucked therethrough;
    a silicon wafer configured to support the puller;
    an insulating layer disposed on a surface of the silicon wafer and a surface of the puller; and
    an electrode layer disposed on a surface of the insulating layer to connect to a first fluid channel disposed on the top of the patch clamp and a second fluid channel disposed on the bottom of the patch clamp,
    wherein the puller is formed in a shape of a pipette through a plurality of reflow processes, and wherein a width of a top part of the puller is less than a width of a bottom part of the puller.

5. The patch clamp of claim 4, wherein the insulating layer is disposed on the surface of the silicon wafer and the surface of the puller.

6. A method of manufacturing a patch clamp, the method comprising:
    a first step of etching a peripheral region of a first type filler while leaving the first type filler in a silicon wafer in a downward direction from a top surface of the silicon wafer;
    a second step of bonding a glass wafer to the top surface of the silicon wafer;
    a third step of forming a first type puller by filling the peripheral region etched in the first step with glass through a reflow process of the glass wafer, wherein the filler of the silicon wafer is positioned at a center of the first type puller;
    a fourth step of etching a peripheral region of the puller in the silicon wafer, after removing the glass wafer present on the top surface of the silicon wafer;
    a fifth step of forming a second type puller from the first type puller by additionally performing a reflow of glass on the first type puller;
    a sixth step of etching the filler of the silicon wafer positioned at a center of the second type puller;
    a seventh step of etching in an upward direction from a bottom surface of the silicon wafer to the bottom of the second type puller;
    an eighth step of disposing an insulating layer on the top surface of the silicon wafer, the bottom surface of the silicon wafer, and a surface of the second type puller; and
    a ninth step of disposing an electrode layer on a surface of the insulating layer.

7. The method of claim 6, wherein a width of the peripheral region etched in the first step corresponds to a width of the second type puller.

8. The method of claim 6, wherein a height of the peripheral region etched in the fourth step corresponds to a height of the second type puller.

* * * * *